US009808602B2

(12) United States Patent
Shaw et al.

(10) Patent No.: US 9,808,602 B2
(45) Date of Patent: *Nov. 7, 2017

(54) NEEDLE RETRACTION APPARATUS

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US); Nl Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/095,716

(22) Filed: Apr. 11, 2016

(65) Prior Publication Data
US 2016/0310705 A1 Oct. 27, 2016

Related U.S. Application Data

(63) Continuation of application No. 13/841,462, filed on Mar. 15, 2013, now Pat. No. 9,308,353, which is a continuation-in-part of application No. 12/846,402, filed on Jul. 29, 2010, now Pat. No. 8,496,600.

(60) Provisional application No. 61/737,263, filed on Dec. 14, 2012.

(51) Int. Cl.
*A61M 25/06* (2006.01)
(52) U.S. Cl.
CPC .... *A61M 25/0631* (2013.01); *A61M 25/0693* (2013.01)

(58) Field of Classification Search
CPC .......... A61M 25/0693; A61M 25/0631; A61M 2025/0681; A61M 25/0606; A61M 25/0612; A61M 5/19; A61M 2005/2006; A61M 2005/2488; A61M 5/32; A61M 5/3276; A61M 2005/342; A61M 5/345
See application file for complete search history.

(56) References Cited

U.S. PATENT DOCUMENTS

| 4,466,446 A | 8/1984 | Baidwan et al. |
| 4,747,831 A | 5/1988 | Kulli |
| 4,813,426 A | 3/1989 | Haber et al. |
| 4,813,935 A | 3/1989 | Haber et al. |
| 4,941,883 A | 7/1990 | Venturini |
| 4,973,316 A | 11/1990 | Dysarz |

(Continued)

FOREIGN PATENT DOCUMENTS

| EP | 0479303 | 8/1992 |
| EP | 1161962 | 12/2001 |

*Primary Examiner* — Nathan R Price
*Assistant Examiner* — Melissa A Snyder
(74) *Attorney, Agent, or Firm* — Monty L. Ross; Ross Barnes LLP; Robin L. Barnes

(57) ABSTRACT

A needle retraction apparatus comprising a body having a forwardly projecting needle, a needle retraction mechanism seated inside the body and biasing the needle rearwardly relative to the body, a slide member attachable to the body and having an opening communicating with a needle retraction cavity projecting away from the body, and an actuator rotatable relative to the slide member to reposition the slide member from a first position preventing needle retraction to a second position permitting needle retraction. An IV catheter introducer comprising the subject needle retraction apparatus is also disclosed.

14 Claims, 5 Drawing Sheets

(56) References Cited

U.S. PATENT DOCUMENTS

| | | |
|---|---|---|
| 5,163,916 A | 11/1992 | Sunderland |
| 5,263,942 A | 11/1993 | Smedley et al. |
| 5,298,023 A | 3/1994 | Haber et al. |
| 5,370,628 A | 12/1994 | Allison et al. |
| 5,395,337 A | 3/1995 | Clemens et al. |
| 5,423,758 A | 6/1995 | Shaw |
| 5,445,618 A | 8/1995 | Adobbati |
| 5,503,010 A | 4/1996 | Yamanaka |
| 5,573,510 A | 11/1996 | Isaacson |
| 5,685,863 A | 11/1997 | Botich et al. |
| 5,704,920 A | 1/1998 | Gyure |
| 5,728,073 A | 3/1998 | Whisson |
| 5,779,679 A | 7/1998 | Shaw |
| 5,795,339 A | 8/1998 | Erskine |
| 5,957,887 A | 9/1999 | Osterlind et al. |
| 5,964,731 A | 10/1999 | Kovelman |
| 6,039,713 A | 3/2000 | Botich et al. |
| 6,063,040 A | 5/2000 | Owen et al. |
| 6,210,371 B1 | 4/2001 | Shaw |
| 6,277,102 B1 | 8/2001 | Carilli |
| 6,468,250 B2 | 10/2002 | Yang |
| 6,808,512 B1 | 10/2004 | Lin et al. |
| 6,974,423 B2 | 12/2005 | Zurcher |
| 7,351,224 B1 | 4/2008 | Shaw |
| 8,292,852 B2 | 10/2012 | Mulholland |
| 8,343,094 B2 | 1/2013 | Shaw |
| 2001/0021827 A1 | 9/2001 | Ferguson et al. |
| 2002/0068907 A1 | 6/2002 | Dysarz |
| 2002/0082560 A1 | 6/2002 | Yang |
| 2003/0078540 A1 | 4/2003 | Saulenas et al. |
| 2003/0171695 A1 | 9/2003 | Zurcher |
| 2003/0181871 A1 | 9/2003 | Wilkinson et al. |
| 2003/0236504 A1 | 12/2003 | Chen |
| 2004/0015135 A1 | 1/2004 | Wilkinson |
| 2004/0019329 A1 | 1/2004 | Erskine |
| 2004/0133172 A1 | 7/2004 | Wilkinson |
| 2004/0204688 A1 | 10/2004 | Lin et al. |
| 2005/0004524 A1 | 1/2005 | Newby et al. |
| 2005/0288607 A1 | 12/2005 | Konrad |
| 2006/0155244 A1* | 7/2006 | Popov ............... A61M 25/0625 604/162 |
| 2006/0189934 A1 | 8/2006 | Kuracina et al. |
| 2006/0235354 A1 | 10/2006 | Kaal et al. |
| 2007/0260189 A1 | 11/2007 | Shaw et al. |
| 2008/0132851 A1 | 6/2008 | Shaw et al. |
| 2008/0132854 A1 | 6/2008 | Sharp |
| 2008/0287881 A1 | 11/2008 | Kiehne |
| 2008/0319345 A1 | 12/2008 | Swenson |
| 2009/0198196 A1 | 8/2009 | West et al. |
| 2009/0306601 A1 | 12/2009 | Shaw et al. |
| 2010/0000040 A1 | 1/2010 | Shaw et al. |
| 2010/0003067 A1 | 1/2010 | Shaw et al. |
| 2010/0241029 A1 | 9/2010 | Mahurkar |
| 2010/0286604 A1 | 11/2010 | Shaw |
| 2011/0264037 A1 | 10/2011 | Foshee et al. |
| 2012/0022464 A1 | 1/2012 | Zivkovic et al. |
| 2012/0071790 A1 | 3/2012 | Mahurkar |
| 2012/0071827 A1 | 3/2012 | Zivkovic et al. |
| 2012/0078225 A1 | 3/2012 | Zivkovic et al. |
| 2012/0226232 A1 | 9/2012 | Shaw et al. |
| 2012/0259243 A1 | 10/2012 | Shaw et al. |
| 2012/0316466 A1 | 12/2012 | Crawford et al. |

* cited by examiner

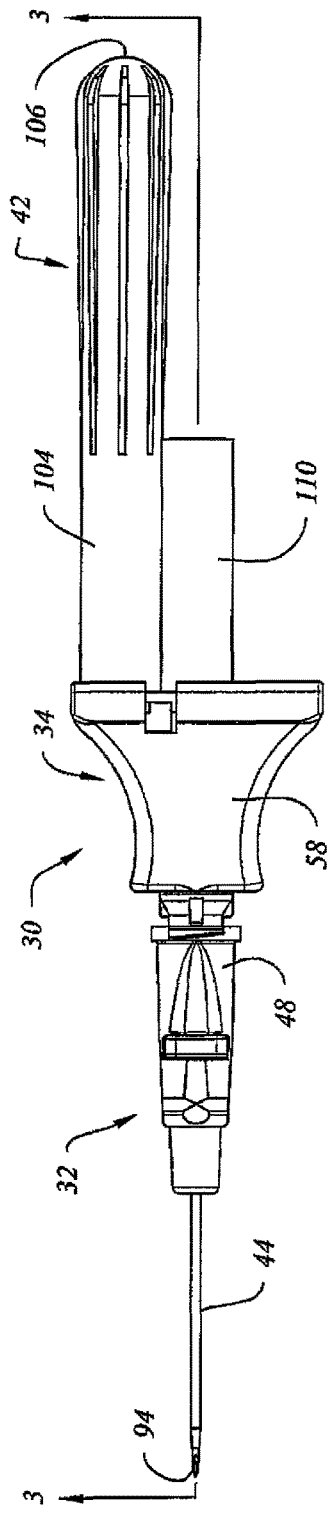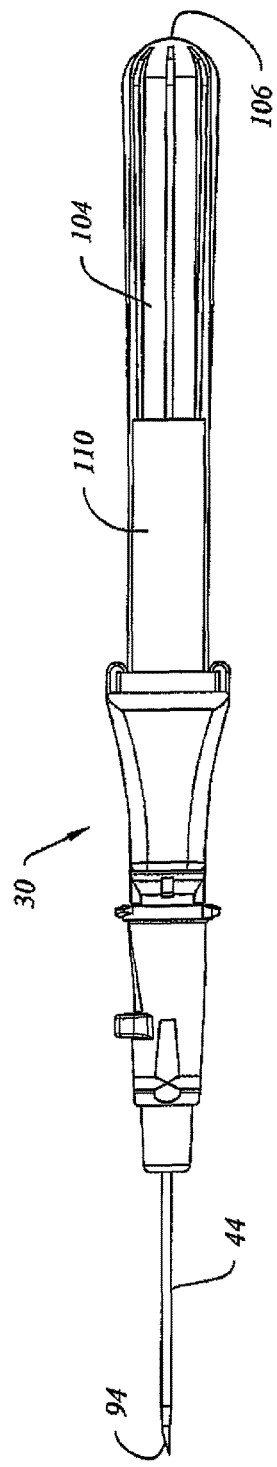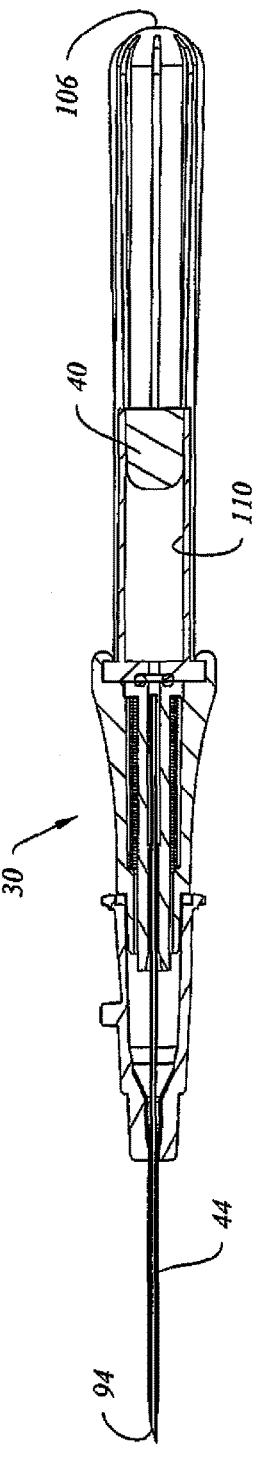

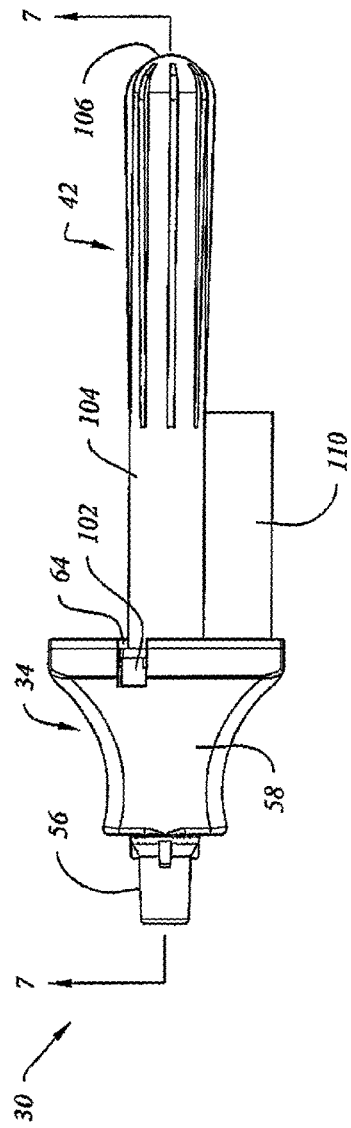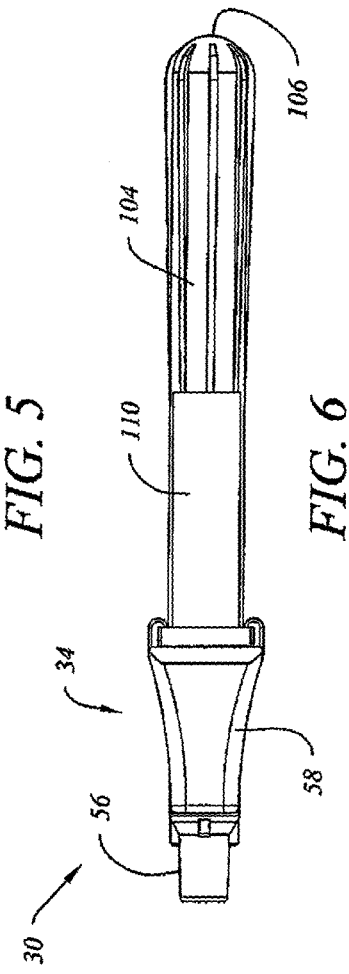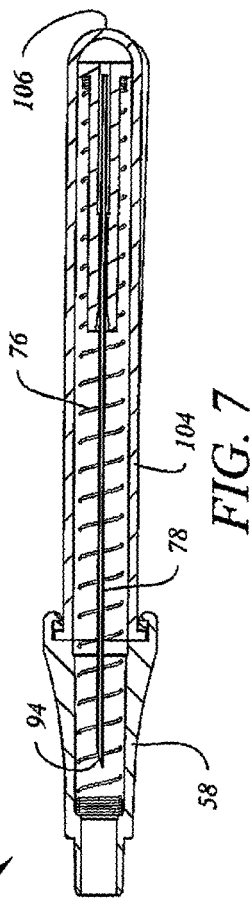

NEEDLE RETRACTION APPARATUS

CROSS-REFERENCE TO RELATED APPLICATION

This application claims the benefit of U.S. Provisional Patent Application No. 61/737,263, filed Dec. 14, 2012. This application is a continuation of U.S. patent application Ser. No. 13/841,462, filed Mar. 15, 2013, now U.S. Pat. No. 9,308,353, and is also a continuation-in part of U.S. patent application Ser. No. 12/846,402, filed Jul. 29, 2010, now U.S. Pat. No. 8,496,600.

BACKGROUND OF THE INVENTION

1. Field of the Invention

This invention relates to a safety needle retraction apparatus for medical devices and, more particularly, to a new safety needle retraction apparatus that is part of a catheter introducer for intravenous or other biomedical applications, or as part of another device useful for other fluid infusion or collection procedures.

One aspect of the invention relates to an IV catheter introducer having a needle retraction apparatus that is rotationally activated. Another aspect of the invention relates to a needle retraction apparatus for a glass or plastic liquid infusion or collection device, the apparatus having a body, a needle retraction mechanism, and a forwardly facing, rearwardly biased needle.

Another aspect of the invention is a retractable needle apparatus that is also adapted to be use with a conventional catheter hub and cannula that are attachable to the front of the apparatus.

Another aspect of the invention relates to a rear slide assembly having a flash chamber and a substantially parallel and laterally spaced-apart needle retraction tube. The rear slide assembly is adapted to move transversely relative to the body as the needle retraction tube is rotated relative to the body to initiate needle retraction following fluid collection or infusion.

Another aspect of the invention relates to a method for retracting a needle in a medical device whereby rotating a needle retraction tube causes the needle retraction tube to be repositioned laterally into coaxial alignment with a rearwardly biased needle to facilitate retraction of the needle into the needle retraction tube.

2. Description of Related Art

U.S. Publ. No. 2006/0155244 to Popov discloses a venipuncture device that rotates a port unit following needle retraction. The needle retraction chamber is disposed inside the medical device and remains stable while the port unit is moved rotationally relative to the retraction chamber following needle retraction. The frontal attachment disclosed there cannot be used with a generic luer lock syringe.

Although many advancements in medical safety technology have been made in recent years, a retractable needle apparatus is needed that can be used in combination with other commercially available fluid collection or infusion devices such as the IV-catheter introducer described here. Such a device will desirably have a needle retraction chamber external to the fluid flow path and will offer the advantages of a retractable needle having sufficient retraction force.

SUMMARY OF THE INVENTION

A needle retraction apparatus is disclosed that comprises a body, a slide member attachable to the rear of the body, a needle retraction mechanism seated inside the body, a fluid seal seated between the body and the slide member, and a medical grade stainless steel (or approved equivalent) needle projecting forwardly from the body. According to one embodiment of the invention, the body comprises a centrally disposed, stepped axial bore, laterally projecting gripping surfaces, and a forwardly projecting nose to which a conventional catheter hub and cannula are releasably attachable.

According to one embodiment of the invention, the slide member comprises a forwardly facing surface that is configured to abut and move transversely in slidable relation to the rear of the body during the needle retraction process. In one embodiment, the rear of the body comprises upper and lower tracks that slidably engage the major transverse portion of the slide member. The slide member desirably further comprises two laterally spaced openings, one of which serves as an opening into a flash chamber projecting rearwardly behind the forwardly facing surface, and another of which serves as an opening for a rearwardly projecting needle retraction tube that is substantially parallel to but spaced laterally apart from the flash chamber.

The flash chamber is desirably aligned initially with the needle holder, and is preferably transparent or sufficiently translucent that medical personnel using the device can readily determine whether vascular access has been achieved during insertion. A polymeric plug or other suitable apparatus is desirably installed at the rear of the flash chamber to facilitate fluid infusion or collection through the flash chamber. The plug can be pierceable or can be provided with a continuous bore to facilitate connection to other fluid collection or infusion apparatus.

The needle retraction tube is desirably supported by the slide member but is rotatable in relation to the slide member to facilitate lateral repositioning of the needle retraction tube during the needle retraction process. According to one embodiment of the invention, the needle retraction tube desirably has an open front end and a closed rear end, and comprises an annular flange disposed around the open end. The annular flange preferably comprises a forwardly projecting lug that is received into a cooperatively aligned positioning notch in the body during assembly. As the needle retraction tube is rotated to initiate needle retraction, the forwardly projecting lug moves arcuately around the longitudinal axis of the retraction tube and engages the sides of the repositioning notch in the body, which causes the slide member to move transversely relative to the body, thereby placing the needle retraction tube in substantially coaxial alignment with the needle holder and needle.

According to one embodiment of the invention, the needle retraction mechanism comprises an elongate needle holder that is receivable into the axial bore of the body and captures a compressed retraction spring inside the body. Other similarly effective means for biasing the needle holder and needle rearwardly can also be used. The needle holder is desirably restrained inside the body prior to needle retraction by the facing and abutting slide member, and a fluid seal is desirably disposed between the rearwardly facing head of the needle holder and a forwardly facing annular recess in the opening into the flash chamber.

The needle retraction apparatus of the invention can be provided separately from or in combination with the catheter hub, but is desirably provided with the catheter hub already installed onto the body. According to one satisfactory method of using the invention, the protective cap (not shown) is removed from the front of the needle and catheter hub, and with the forwardly projecting lug of the needle retraction tube positioning the flash chamber in substantially coaxial alignment with the needle holder and needle, the needle is inserted into a patient. If blood appears in the flash chamber, this signifies successful vascular insertion. The needle can be retracted from the cannula and into the apparatus by rotating the needle retraction tube relative to the body to reposition the needle retraction tube into coaxial alignment with the needle holder. Once the point of coaxial alignment is reached, the rearwardly biased needle holder is propelled rearwardly into a retraction cavity inside the needle retraction tube. At this point the catheter hub is available for connection to another apparatus such as an IV set.

BRIEF DESCRIPTION OF THE DRAWINGS

The apparatus of the invention is further described and explained in relation to the following drawings wherein:

FIG. 1 is a top plan view of one embodiment of an apparatus of the invention with the needle projecting forwardly from the needle hub of the apparatus in coaxial alignment with the flash chamber tube of the apparatus;

FIG. 2 is a side elevation view the embodiment of FIG. 1;

FIG. 3 is a cross-sectional side elevation view taken along line 3-3 of FIG. 1;

FIG. 5 is a cross-sectional top plan view of the embodiment of FIG. 1 with following needle retraction and with the needle retraction tube repositioned into coaxial alignment with the needle hub;

FIG. 6 is a side elevation view of the embodiment of FIG. 5; and

FIG. 7 is a cross-sectional side elevation of the embodiment of FIG. 1 showing the needle holder and at least a portion of the needle and retraction spring retracted into the needle retraction cavity;

DESCRIPTION OF THE PREFERRED EMBODIMENTS

Figure 4:
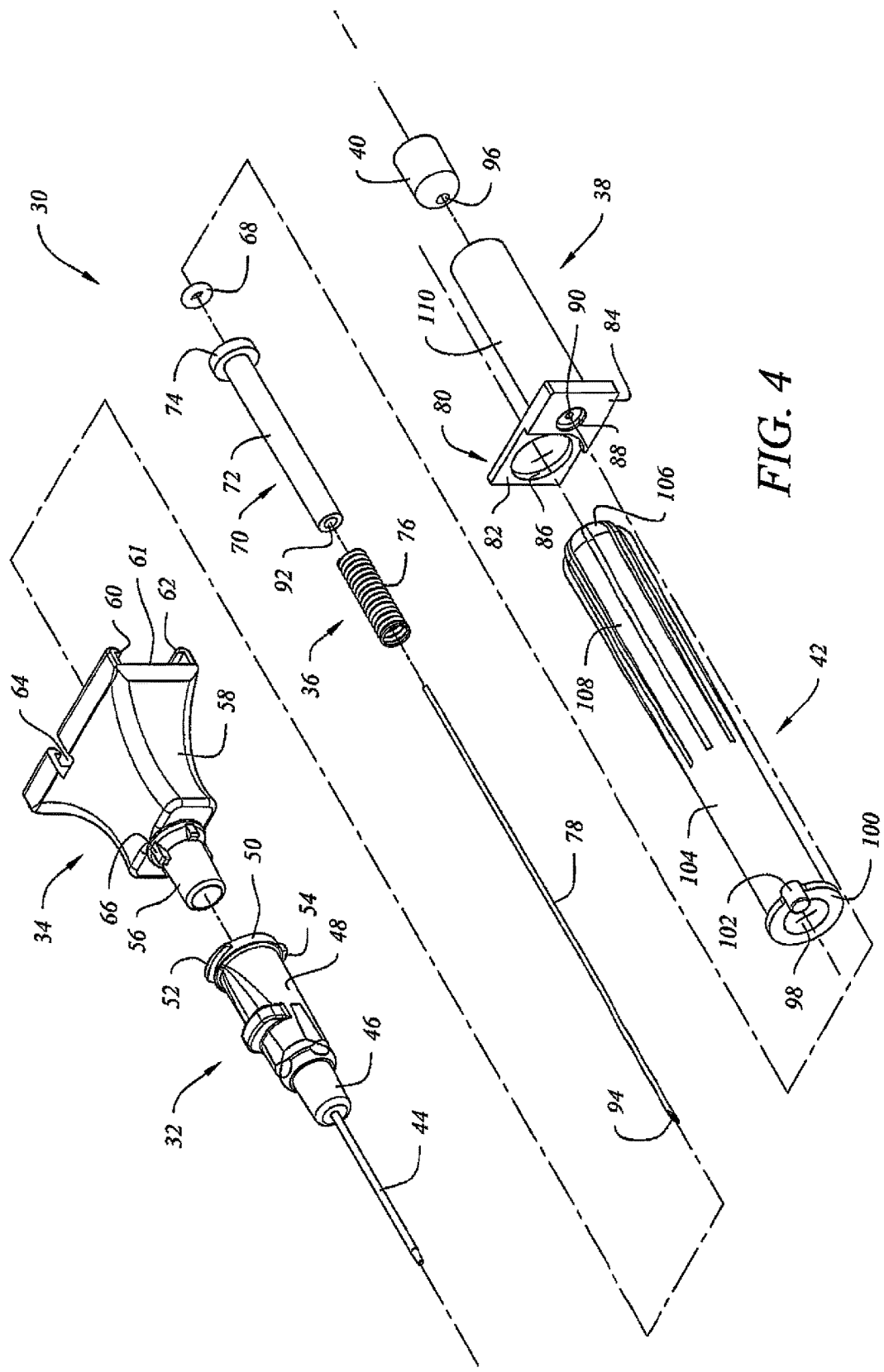
FIG. 4 is an exploded front perspective view of the embodiment of FIG. 1.
Figure 8:
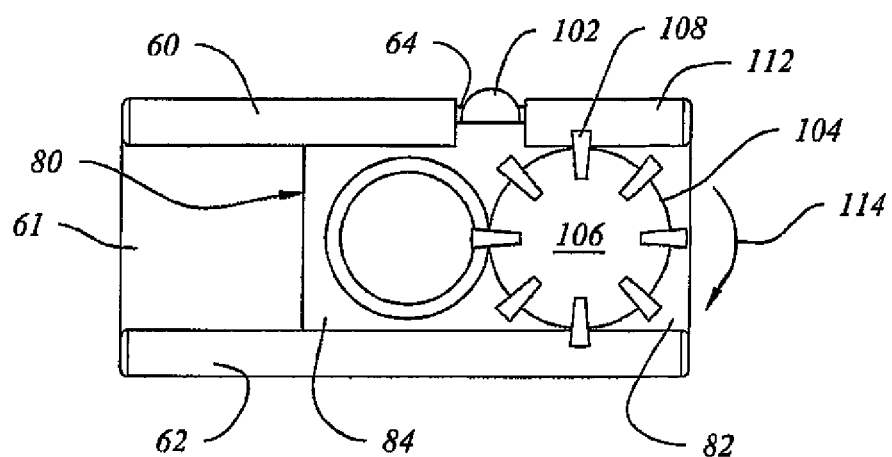
FIG. 8 is a rear elevation view of the apparatus of FIG. 1.
Figure 9:
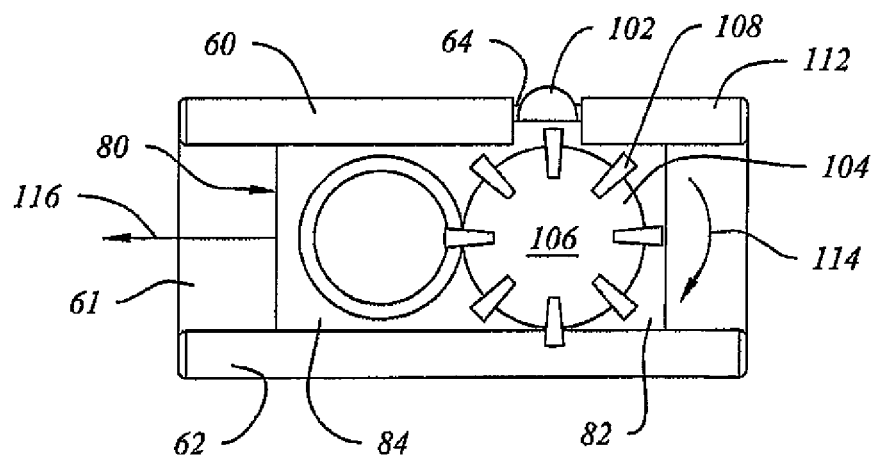
FIGS. 9 and 10 are rear elevation views of the of the apparatus of FIG. 1 wherein the needle retraction tube has been rotated sufficiently to cause the rear slide assembly to begin repositioning the needle retraction tube into coaxial alignment with the needle holder.
Figure 10:
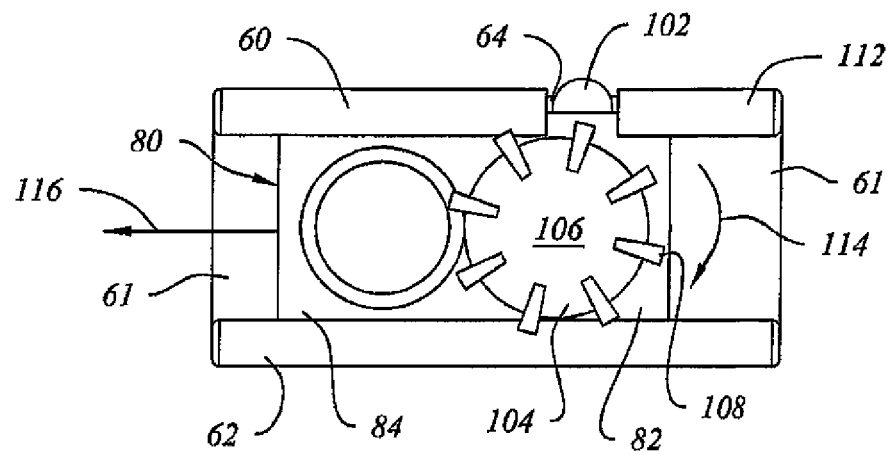
Figure 11:
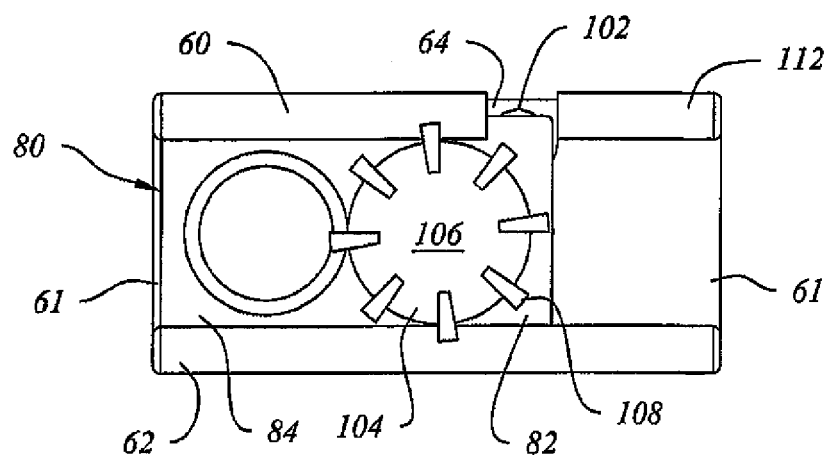
FIG. 11 is a rear elevation view of the apparatus of FIG. 1 with the needle retraction tube fully repositioned to the retraction position.

FIGS. 1-4 disclose an IV catheter introducer 30 that comprises the needle retraction apparatus of the invention, which further comprises body 34, forwardly projecting needle 78 (FIG. 4) with beveled tip 94, needle retraction mechanism 36, slide member 38, and needle retraction tube 42. Referring to FIGS. 1-4, catheter hub assembly 32 is a conventional IV catheter hub that is releasably attachable to body 34 and includes a forwardly facing flexible sheath or cannula 44 through which needle 78 is inserted to facilitate vascular insertion. Needle retraction mechanism 36 is seated inside body 34, and is held in place by slide member 38 (FIG. 4) into which needle retraction tube 42 is inserted prior to being slidably engaged with the rear of body 34 during assembly. It will also be appreciated by those of ordinary skill in the art upon reading this disclosure that the needle retraction apparatus of the invention is readily adaptable for use with other medical devices in which a retractable needle and a rotationally activated needle retraction mechanism are desired.

As depicted, catheter hub 32 further comprises hub nose 46 projecting forwardly from substantially cylindrical barrel 48 that also has a rear opening surrounded by annular attachment collar 50 comprising opposed lugs 52, 54. The inside of annular attachment collar 50 and barrel 48 desirably comprises a tapered female luer surface configured to provide fluid-tight frictional engagement with forwardly projecting male luer tip 56 of body 34.

Body 34 comprises a stepped inside surface (FIG. 3) and has outside gripping surfaces 58 desirably configured to be easily graspable by a clinician during vascular insertion. The rear portion of body 34 preferably comprises laterally extending upper track 60 and lower track 62 that are desirably configured to slidably engage and retain forwardly facing frame 80 of slide member 38 in close proximity to body 34. A positioning notch 64 is desirably provided at the rear of body 34 to facilitate engagement with forwardly projecting lug 102 of needle retraction tube 42 as further described below in relation to operation of the device.

Needle retraction mechanism 36 comprising needle holder 70 and spring 76 (depicted in its compressed state to save space for illustrative purposes in FIG. 4 rather than relaxed as shown in FIG. 7) is desirably seated in the stepped cylindrical interior of body 34. Needle holder 70 as shown comprises elongate cylindrical shaft 72 and a larger-diameter head 74. The outside diameter of shaft 72 is desirably slightly less than the inside diameter of coiled spring 76 to permit insertion of shaft 72 through the coiled spring. A continuous axial bore 92 desirably extends through shaft 72 and head 74 of needle holder 70. The outside diameter of head 74 is desirably sufficiently larger than that of shaft 72 to provide a forwardly facing annular surface at the rear end of shaft 72 against which the rear end of spring 76 abuts when compressed and installed inside body 34. The rearwardly facing end of the head 74 of needle holder 70 can comprise a slight recess to facilitate seating of fluid seal 68, although fluid seal 68 is desirably carried by slide member 38 during needle retraction as discussed below. Compressed spring 76 biases needle holder 70 rearwardly in relation to body 34, and needle holder 70 is retained inside body 34 against the spring bias by slide member 38 when slide member 38 is assembled to body 34. Although spring 76 is satisfactory for use in biasing needle holder rearwardly in relation to body 34, other similarly effective configurations can also be used. During assembly of the subject needle retraction apparatus, the rearwardly facing blunt end of needle 78 (FIG. 4) is desirably inserted into bore 92 of needle holder 70 from the front and is attached in fixed relation to needle holder 70 by any known suitable means, such as by gluing or the like.

Slide member 38 desirably comprises frame 80 and rearwardly projecting, substantially cylindrical fluid flash chamber 110 having an interior space into which fluid can flow from a patient through needle 78, needle holder 70 and aperture 90. Elastomeric plug 40 is desirably fitted into a rearwardly facing opening of flash chamber 110. The forwardly facing portion of slide member 38 desirably comprises first and second circular openings including apertures 90, 86, respectively. Opening 90 is provided rearwardly of annular recess 88 in forwardly facing surface 84. Annular recess 88 is provided for seating fluid seal 68, which is preferably an elastomeric O-ring disposed between head 74 of needle holder 70 and slide member 38 to prevent fluid leakage during use and prior to needle retraction. Aperture 86 is provided in recessed surface section 82 to facilitate assembly of needle retraction tube 42 with slide member 38.

Needle retraction tube 42 desirably comprises a first tubular section 104 having a forwardly facing open end 98 surrounded by radially projecting annular collar 100, and a second tubular section 108 having a closed end 106 projecting away from body 34. The substantially cylindrical interior space of needle retraction tube 42 serves as a retraction cavity. A plurality of ribs (or other similarly effective surface texturing) are desirably provided around section 108 to facilitate gripping needle retraction tube 42 to rotate needle retraction tube 42 relative to body 34 to initiate needle retraction. Forwardly projecting lug 102 is desirably provided at the front of needle retraction tube 42, and is desirably cooperatively aligned with positioning notch 64 in body 34. During assembly, needle retraction tube 42 is desirably inserted into aperture 86 from the front of slide member 38 so that tube 42 is rotatable around its longitudinal axis when mounted in slide member 38 and so that the front face of annular collar 100 (except for lug 102) is substantially flush with forwardly facing surface 84 of slide member 38.

Referring to FIGS. 1-3, when IV catheter introducer 80 is fully assembled, and ready for use (with the needle cap removed), beveled needle tip 94 projects forwardly from cannula 44 and the central longitudinal axis of flash chamber 110 is aligned with the longitudinal axis of the needle. Referring to FIGS. 5-7 and 8-11, when needle retraction tube 42 is rotated relative to body 34 as indicated by arrow 114, the forwardly projecting lug 102 pushes against the side. of positioning notch 64 of body 34 and causes slide member 38 to slide relative to body 34 in the direction indicated by arrow 118. As slide member 38 moves laterally relative to body 34, fluid seal 68 (FIG. 4) disengages from head 74 of needle holder 70, eventually reaching the position shown in FIGS. 5-7 and 11 wherein the central longitudinal axis through needle retraction tube 42 is aligned with needle holder 70. Because the diameter of front opening 98 of retraction tube 42 (FIG. 4) is slightly larger than the outside diameter of head 74 of needle holder 70, the force of expanding spring 76 (FIG. 4) propels needle holder 70 and needle 78 rearwardly into needle retraction tube 42.

Those of ordinary skill in the art will also appreciate upon reading this specification and the description of preferred embodiments disclosed here that modifications and alterations to the apparatus and method of use can be made within the scope of the invention and it is intended that the scope of the invention be limited only by the broadest interpretation of the appended claims to which the inventors are legally entitled.

The invention claimed is:

1. A needle retraction apparatus comprising:
a body having a forwardly projecting needle;
a needle retraction mechanism seated inside the body and biasing the needle rearwardly relative to the body;
a slide member disposed rearwardly of the body and attached in slidable engagement to the body and having a first opening communicating with a needle retraction cavity projecting away from the body; and
a needle retraction tube containing the needle retraction cavity, the needle retraction tube being supported by the slide member and rotatable relative to the slide member and the body to reposition the slide member from a first position preventing needle retraction to a second position permitting needle retraction into the needle retraction cavity;
wherein the slide member is configured to move transversely relative to the body between the first position and the second position.

2. The needle retraction apparatus of claim 1 wherein the body further comprises a forwardly projecting luer tip.

3. The needle retraction apparatus of claim 2 in combination with an IV catheter comprising a hub that is releasably attached to the luer tip and a flexible cannula attached to the hub through which the needle projects forwardly of the hub.

4. The needle retraction apparatus of claim 1 wherein the needle retraction mechanism comprises a needle holder seated inside the body.

5. The needle retraction apparatus of claim 4 wherein the needle is attached to the needle holder and is biased rearwardly by a compressed needle retraction spring contacting the needle holder.

6. The needle retraction apparatus of claim 1 wherein the body comprises spaced-apart tracks that cooperate with the slide member to retain the slide member in close sliding engagement with the body.

7. The needle retraction apparatus of claim 5 wherein the slide member further comprises a rearwardly projecting flash chamber and a second opening providing fluid communication between the needle holder and the flash chamber.

8. The needle retraction apparatus of claim 7 wherein the rearwardly projecting flash chamber has a closed end that is distal to the second opening.

9. The needle retraction apparatus of claim 8 wherein the closed end of the flash chamber is blocked by an elastomeric plug.

10. The needle retraction apparatus of claim 9 wherein the elastomeric plug is penetrable by a cannula to establish a fluid path through the closed end of the flash chamber.

11. The needle retraction apparatus of claim 1 wherein the needle retraction tube is receivable through the first opening in the slide member.

12. The needle retraction apparatus of claim 11 wherein the needle retraction tube has an open end with and a closed end, and a radially projecting annular flange around the open end that has a diameter larger than the first opening of the slide member and is supported in a forwardly facing recess in the slide member.

13. The needle retraction apparatus of claim 1 wherein the needle retraction tube comprises a projecting lug that engages a positioning notch in the body.

14. The needle retraction apparatus of claim 1 configured as an IV-catheter introducer.

* * * * *